(12) United States Patent
Bucur et al.

(10) Patent No.: US 10,340,033 B2
(45) Date of Patent: Jul. 2, 2019

(54) AUTONOMOUS LINKAGE OF PATIENT INFORMATION RECORDS STORED AT DIFFERENT ENTITIES

(75) Inventors: Anca Ioana Daniela Bucur, Eindhoven (NL); Richard Vdovjak, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 594 days.

(21) Appl. No.: 13/499,989

(22) PCT Filed: Sep. 29, 2010

(86) PCT No.: PCT/IB2010/054390
§ 371 (c)(1),
(2), (4) Date: Apr. 3, 2012

(87) PCT Pub. No.: WO2011/042838
PCT Pub. Date: Apr. 14, 2011

(65) Prior Publication Data
US 2012/0203576 A1    Aug. 9, 2012

(30) Foreign Application Priority Data
Oct. 6, 2009 (EP) ................................. 09172309

(51) Int. Cl.
*G16H 10/60*     (2018.01)
*G06Q 10/06*     (2012.01)

(52) U.S. Cl.
CPC ............ *G16H 10/60* (2018.01); *G06Q 10/06* (2013.01)

(58) Field of Classification Search
CPC ...... G06Q 50/22; G06Q 50/24; G06F 19/322; G06F 19/327; G16H 10/60
(Continued)

(56) References Cited

U.S. PATENT DOCUMENTS 6,523,019 B1    2/2003    Borthwick
2002/0007284 A1    1/2002    Schurenberg et al.
(Continued)

FOREIGN PATENT DOCUMENTS

JP    2002055857 A    2/2002
JP    2003044660 A    2/2003
(Continued)

OTHER PUBLICATIONS

Zhu, Vivienne J., "An Empiric Modification to the Probabilistic Record Linkage Algorithm Using Frequency-Based Weight Scaling," Journal of the American Medical Informatics Association, vol. 16 No. 5, Sep./Oct. 2009.*
(Continued)

*Primary Examiner* — Elaine Gort
*Assistant Examiner* — John P Go

(57) ABSTRACT

A system for linking corresponding patient information records is disclosed. A plurality of entities (1,1a) have respective patient databases comprising patient information records (3, 3a). Each entity (1, 1a) has associated therewith a patient identification algorithm (4,4a) for matching corresponding patient information records (3, 3a) of the same patient at different entities (1,1a). A linking subsystem (6) maintains a set of links (7) of a first entity (1) of the plurality of entities (1,1a). The linking subsystem (6) is arranged for linking patient information records (3) of the first entity (1) with corresponding patient information records (3a) of the other entities (1a). A link (ID, RID, RLoc) is established when a given patient information record (3) of the first entity (1) matches a corresponding patient information record (3a) of another entity (1a) based on the patient identification algorithm (4) of the first entity (1). The links provide an association between locally-assigned patient identifiers (ID, RID) of the same patient at different entities (1,1a).

16 Claims, 2 Drawing Sheets

(58) Field of Classification Search
USPC .......................................................... 705/2, 3
See application file for complete search history.

(56) References Cited

U.S. PATENT DOCUMENTS

| | | | | |
|---|---|---|---|---|
| 2003/0126102 | A1* | 7/2003 | Borthwick | 706/21 |
| 2004/0128165 | A1* | 7/2004 | Block et al. | 705/2 |
| 2004/0128262 | A1* | 7/2004 | Nafousi | G06Q 30/0283 705/400 |
| 2005/0154615 | A1* | 7/2005 | Rotter et al. | 705/3 |
| 2005/0246205 | A1* | 11/2005 | Wang et al. | 705/3 |
| 2006/0271401 | A1* | 11/2006 | Lassetter | G06Q 10/10 705/2 |
| 2006/0287890 | A1* | 12/2006 | Stead | G16H 10/60 705/3 |

FOREIGN PATENT DOCUMENTS

| | | | |
|---|---|---|---|
| JP | 2003519828 A | 6/2003 | |
| JP | 2008527477 A | 7/2008 | |
| JP | 2008204378 A | 9/2008 | |
| WO | 03021485 A2 | 3/2003 | |
| WO | WO-03021485 A2 * | 3/2003 | G06Q 50/24 |

OTHER PUBLICATIONS

Grannis, Shaun J., Privacy and Security Solutions for Interoperable Health Information Exchange, Jun. 30, 2009, Perspectives on Patient Matching: Approaches, Findings, and Challenges.*

Grannis, "Privacy and Security Solutions for Interoperable Health Information Exchange—Perpectives on Patient Matching: Approaches, Findings, and Challenges," Jun. 30, 2009, The Office of the National Coordinator for Health Information Technology.*

Grannis, Shaun J., "Privacy and Security Solutions for Interoperable Health Information Exchange," Jun. 30, 2009.*

Grannis, Shaun, "Privacy and Security Solutions for Interoperable Health Information Exchange—Perspectives on Patient Matching: Approaches, Findings, and Challenges," Jun. 3, 2009 (Year: 2009).*

Zhu et al, "An Empiric Modification to the Probabilistic Record Linkage Algorithm Using Frequency-Based Weight Scaling", Journal of the American Medical Informatics Association (JAMIA), vol. 16, No. 5, Sep. 1, 2009.

Grannis et al, "Privacy and Security Solutions for Interoperable Health Information Exchange—Perspectives on Patient Matching: Approaches, Findings, and Challenges", The Office of the National Coordinator for Health Information Technology, Jun. 30, 2009, 57 Pages.

Yakout et al, "Efficient Private Record Linkage", IEEE International Conference on Data Engineering, 2009, pp. 1283-1286.

Agrawal, R. et al. "Securing electronic health records without impeding the flow of information", Int. J. Med. Inform., 2007.

Wang, C. et al. "A CORBA-based object framework with patient identification translation and dynamic linking. Methods for exchanging patient data", Methods of information in medicine, 1999, 38(1): 56-65.

Al-Lawati, A. et al. "Blocking-aware private record linkage", Ali Al-Lawati et al., IQIS, 2005 Criteria.

* cited by examiner

AUTONOMOUS LINKAGE OF PATIENT INFORMATION RECORDS STORED AT DIFFERENT ENTITIES

FIELD OF THE INVENTION

The invention relates to linking corresponding patient information records stored at different entities.

BACKGROUND OF THE INVENTION

Typically, patients can receive care from multiple healthcare providers geographically dispersed at multiple sites. At each site, the patient is usually given a different patient identifier. This patient identifier may be used locally at the healthcare provider. Moreover, the patient data of a single patient, such as medical images and other relevant medical information, is spread across multiple sites and labeled with different local patient identifiers. In order to be able to retrieve the patient data stored elsewhere, the patient identifiers are reconciled and the respective patient records are linked together.

Over time, the average volume of data collected for a patient in the context of a complex disease such as cancer has increased tremendously. For example, for recurring cancer patients, a large part of the medical history can be relevant to a clinician. In the case of recurring cancer patients, the relevant cancer-related health episodes can go back many years. Co-morbidities are often relevant as well, as they are a very constraining factor in choosing a therapy. For example, many chemotherapy agents are cardio-toxic, and in order to choose the right therapy, prior information concerning cardiac disease may be important. It is highly unlikely that the information about all these health-related episodes resides in the system of a single institution. However, the treating clinician seeing a patient should be able to extract all the relevant prior health episodes from the patient record, both cancer- and non-cancer-related, which may include many episodes and span decades.

The flow of information into and out of the patient record is typically channeled through a Master Patient Index (MPI) that assigns a unique medical record number (MRN) to each patient of an entity when a unit record exists. Herein, the unit record comprises the actual patient data maintained by the entity. It can be the electronic health record of the patient, the patient record in the radiology information system (RIS) and all the other patient data (such as studies, images, lab data) maintained by that entity. All the data items of a unit record may be linked by the locally assigned patient identifier (e.g., MRN). To obtain a view of patients across distributed data sources, the local identifiers in the individual institutions are reconciled. This is currently done by building an Enterprise-wide Master Patient Index (EMPI) that interrelates all the identifiers in the hospitals that are part of the enterprise. The EMPI is developed through integration of the individual MPIs of the sources. Generally, the integration is achieved by comparing demographic attributes such as first/last name, gender, date of birth, address etc., to create an enterprise-level identifier. The integration is rarely based on a single identifier shared across the different organizations in the enterprise. Most of the existing systems deploy probabilistic algorithms which typically compare a fixed record with a number of candidates for a match, computing for each candidate a likelihood ratio (weighted score) that is compared to chosen accept and reject thresholds. The result is used to decide whether to link the records or not. When the decision cannot be taken automatically (the computed likelihood falls in between the two thresholds), qualified personnel need to review or flag the potential (mis)matches before they are accepted (or rejected). The manual review of uncertain matches helps to minimize linkage errors as they can have far-reaching consequences, ultimately endangering a patient's health. However, submitting a large amount of records for manual review is very costly and may make the entire solution impractical.

The paper "Efficient Private Record Linkage" by Mohamed Yakout et al., IEEE International Conference on Data Engineering, 2009, pp. 1283-1286 discloses a protocol for private record linkage that makes no use of a third party. The protocol consists of two phases. In phase 1, candidate pairs of records for matching are produced. In phase 2, the task of computing a Euclidean distance between each candidate pair is completed. Both parties participate in the Euclidean distance computations without revealing the original representations of their respective records.

SUMMARY OF THE INVENTION

It would be advantageous to have an improved system for linking corresponding patient information records at different entities. To better address this concern, a first aspect of the invention provides a system comprising:

a plurality of entities having respective patient databases comprising patient information records, each entity having associated therewith a patient identification algorithm for matching corresponding patient information records of the same patient at different entities; and a linking subsystem for maintaining a set of links of a first entity of the plurality of entities, the linking subsystem being arranged for linking patient information records of the first entity with corresponding patient information records of the other entities, a link being established when a given patient information record of the first entity matches a corresponding patient information record of another entity, based on the patient identification algorithm of the first entity.

By associating separate patient identification algorithms with the different entities, the entities do not have to agree on a single patient identification strategy. Consequently, the flexibility of linking is improved. The different patient identification algorithms allow the entities to apply different policies regarding the linking of patient records. This may be used to keep the entities' record linking autonomous by letting the entities choose their own patient identification algorithms.

The links may be arranged to provide an association between locally-assigned patient identifiers of the same patient at different entities. The patient information records at a remote site may be uniquely determined by the patient identifier given to the patient information records at that remote site. Moreover, the patient information records of the first entity may also have unique patient identifiers. Consequently, a link between any patient record of the first entity and any patient record of the other entity may comprise the patient identifiers of the two patient information records. This is a suitable way of specifying a link. Additionally, an identification of the other entity may be included, so that it is clear to which entity the patient identifier belongs.

The system may comprise a further linking subsystem for maintaining a further set of links of a second entity of the plurality of entities, based on the patient identification algorithm of the second entity. The set of links of the second entity is independent of the set of links generated by the first entity. Both entities are autonomous as to the criteria used in matching their patient information records with those of other entities. Still, the entities can crosslink a patient information record, if both entities decide to make a link between the same pair of patient information records.

An entity of the plurality of entities, for example the first entity, may be arranged for storing a local copy of information of the other entities. In particular, the entity may be arranged for storing the information that is used by the patient identification algorithm of that entity for matching the patient information records. This reduces the amount of necessary data communication, because it is possible to apply the patient identification algorithm with locally stored information.

The system may comprise a central repository for storing a copy of the information used by the patient identification algorithms of the plurality of entities for matching the patient information records. This reduces the amount of storage necessary, as any local copies of this information are not necessary.

The system may comprise an initialization subsystem for initially setting up the set of links for at least one of the plurality of entities, processing substantially all available patient information records of that one of the plurality of entities, at least insofar as the available patient information records potentially have corresponding patient information records at the other entities. This way, the links are available at once, which may avoid confusion as to whether additional data exists for a patient or not. Moreover, any inconsistencies may be avoided.

The linking subsystem may be arranged for periodically updating the set of links. This way, the updating may be scheduled at off-hours. Moreover, the set of links is kept up-to-date. Alternatively or additionally, the linking subsystem may be arranged for updating the set of links on demand or each time a new patient identifier is generated at one of the entities. On-demand updating provides flexibility. Updating each time a new patient identifier is generated keeps the links highly up-to-date.

The patient identification algorithm may be based on matching patient demographic data. Patient demographic data is highly useful in distinguishing between patients. The demographic data may include at least one of: name, address, social security number, personal id number, tax number, age, date of birth, sex. Other data types are not excluded.

The patient identification algorithm may include one or more thresholds which are specific for the entity associated with the patient identification algorithm. By setting thresholds differently, an entity may implement a particular patient matching policy.

A medical workstation may be part of an entity of the plurality of entities of the system set forth. The medical workstation may comprise a display for displaying patient information from a patient information record of another entity which is linked with a patient information record of the entity comprising the workstation, the linking having been performed by the linking subsystem.

Another aspect of the invention provides a method of linking corresponding patient information records at different entities, each entity having respective patient databases comprising patient information records, each entity having associated therewith a patient identification algorithm for matching corresponding patient information records of the same patient at different entities, the method comprising maintaining a set of links of a first entity of the plurality of entities, the set of links linking patient information records of the first entity with corresponding patient information records of the other entities, a link being established when a given patient information record of the first entity matches a corresponding patient information record of another entity, based on the patient identification algorithm of the first entity.

Another aspect of the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful. Modifications and variations of the image acquisition apparatus, the workstation, the system, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

It is more and more common that patients receive care from multiple healthcare providers geographically dispersed at multiple sites. This may result in the situation that the patient is usually given multiple patient identifiers, because a new patient identifier is assigned to the patient every time he or she registers at a different healthcare provider. Moreover, patient data such as medical images and other relevant medical information of a patient is collected and stored at multiple sites. However, data collected and stored at one healthcare provider may be needed at another healthcare provider for purposes of diagnosis or treatment. In order to be able to retrieve the patient data stored elsewhere, the patient identifiers at the various sites may be reconciled and linked together. It may be beneficial if this reconciliation and/or linking can be performed without adopting a common patient identifier at the different sites.

Currently this reconciliation and/or linking may be achieved by using identity matching algorithms to link together records in distinct systems that belong to the same patient. Identity matching approaches currently used, both probabilistic and rule-based, assume that the matching should be identical at all sites and a federation-wide single view on the matching results is sufficient. However, in practice this is not necessarily the case. Autonomous healthcare organizations may agree to share patient data, without necessarily agreeing on the same view with respect to patient record matching. The matching process is tuned by trading off data consistency versus completeness, and in the prior art systems, different sites are not able to choose different trade-offs.

The known identity reconciliation approaches may be extended by allowing different organizations to have different identity matching algorithms (also with respect to attribute weights and thresholds), which may result in different mappings, addressing the reconciliation requirements stemming from a distributed heterogeneous environment in which the providers may wish to remain autonomous while still being able to share patient data.

Figure 1:
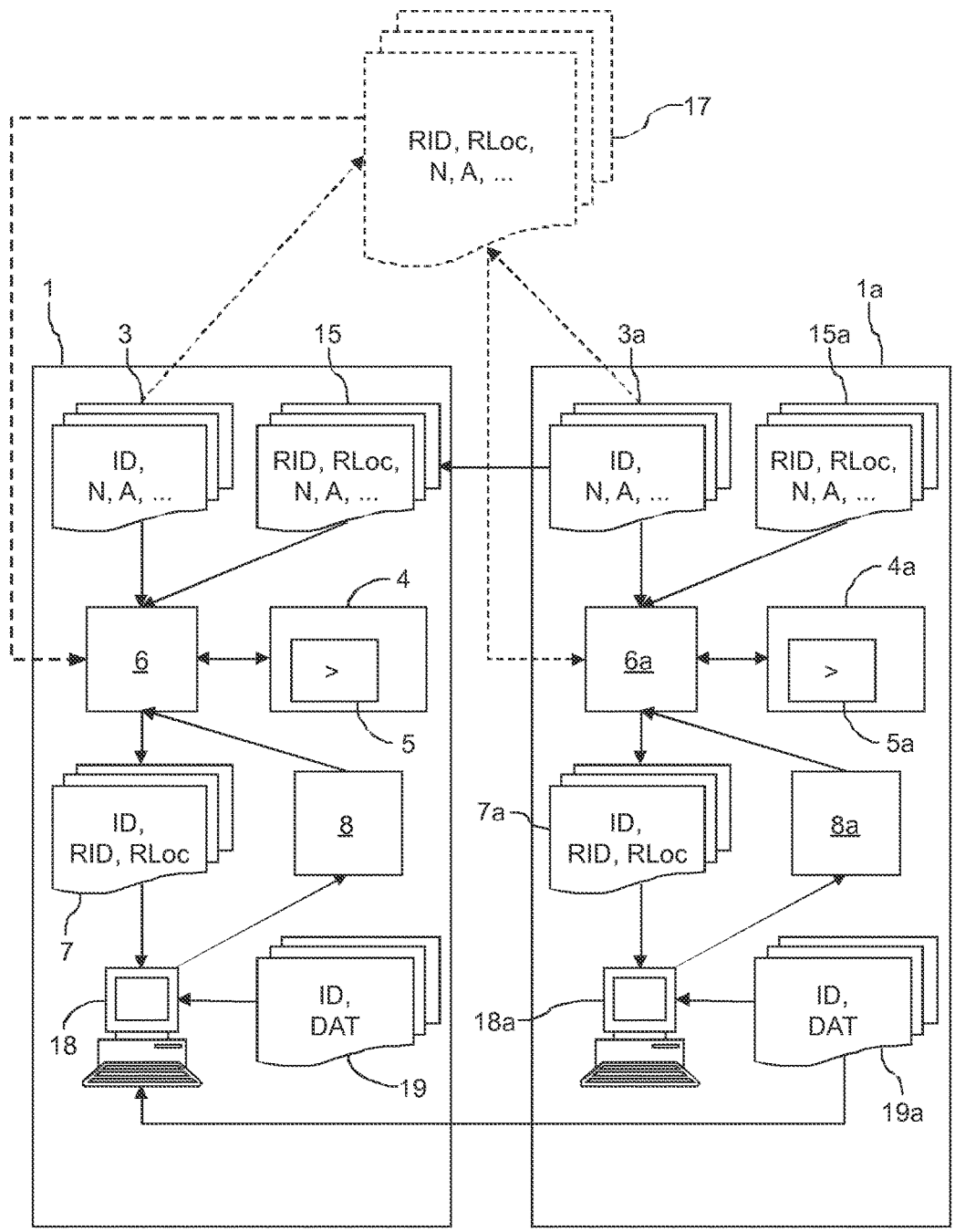
FIG. 1 is a diagram of a system for linking corresponding patient information records stored at different entities.

FIG. 1 illustrates a system for linking corresponding patient information records 19,19a stored at different entities 1,1a. The system comprises a plurality of entities 1,1a. Such an entity may comprise a plurality of computers connected via a network. An entity may also comprise a server system on which a patient data storage system has been installed. The system may thus comprise storage means, a user interface for controlling the system, a data communication port such as a network port, and/or a connection to a wide area network. The different entities may be interconnected by means of the wide area network. The wide area network may be the Internet. In the drawing, two entities 1,1a are shown to illustrate a working example. However, any number of entities is possible by straightforward extension of the techniques described herein. Moreover, what is described herein by way of example for one of the entities 1 or 1a may also be applied to other entities in the system, including entity 1 and/or 1a.

The entities 1,1a may have respective patient databases. These databases comprise patient information records 3,3a. For example, the patient information records 3 of the database of entity 1 may comprise a patient identifier (ID), patient name (N), patient address (A), and/or other demographic information ( . . . ). Moreover, other medical data (DAT), such as images and/or laboratory results and/or medication information, may be stored in separate records 19 which are linked to the demographic information (N, A, . . . ) by means of the patient identifier (ID). Alternatively, these additional data (DAT) may also be stored in the patient record 3 together with the demographic information (N, A, . . . ).

The entity 1 has associated therewith a patient identification algorithm 4. This patient identification algorithm 4 may be used in the process of matching corresponding patient information records of the same patient at different entities. To this end, the patient identification algorithm 4 may comprise a number of comparison operations. Moreover, the patient identification algorithm 4 may comprise one or more probability or likelihood estimates, which may be correlated with the probability that two patient records match. The results of these comparisons and/or estimates may be used in association with one or more threshold values 5. These threshold values 5 may, for example, determine the minimal probability or similarity level necessary to establish a match between two patient records 3 and 3a.

The system may further comprise a linking subsystem 6,6a. Separate linking subsystems 6,6a may be implemented as independent units in the different entities 1,1a, as shown in FIG. 1. However, this is not a limitation. In an alternative example, the linking subsystem can be implemented as a centralized service (not shown). Such a centralized service may be arranged for maintaining the sets of links 7,7a of the entities 1,1a, taking into account the respective patient identification algorithms 4,4a.

In the example arrangement of FIG. 1, the linking subsystem 6 of entity 1 is arranged for maintaining a set of links 7 of entity 1. The linking subsystem 6 may link patient information records 3 of the entity 1 with corresponding patient information records 3a of entity 1a. Likewise, the linking subsystem 6 may link the patient information records of entity 1 with corresponding patient information records of any of the other entities (which are not shown in the Figure). A link may be established when a given patient information record 3 of entity 1 matches a corresponding patient information record 3a of another entity 1a, based on the patient identification algorithm 4 of entity 1. For example, corresponding fields (N, A, . . . ) of the patient information records 3,3a may be compared; if they match, a link may be established. If the match is not perfect, because the patient information records 3,3a differ slightly, the patient identification algorithm 4 and its optional thresholds 5 may represent the policy of whether to establish the link or not. Consequently, the decision of whether to establish a link may be made automatically, at least in a majority of cases. The patient identification algorithm 4 may also result in a decision that the identification algorithm 4 is not able to make the final decision; in such a case, a human operator may evaluate the data and possibly obtain a correction or any further relevant information, for example by asking the patient. Such decisions of the patient identification algorithm are forwarded to the linking subsystem 6, which acts accordingly by, as the case may be, generating a link 7 or putting the patient records on a list for review by a human operator.

The links 7 may provide an association between locally-assigned patient identifiers of the same patient at different entities. For example, a link 7 may comprise an identifier (ID) from the local patient information record 3 as stored by the entity 1, and a "remote" identifier (RID) from the patient information record 3a of the other entity 1a. In case the remote identifier (RID) is not guaranteed to be unique across the plurality of entities, the remote identifier (RID) is not guaranteed to uniquely identify the remote patient information record 3a. Consequently, the link 7 may further comprise an entity identifier (RLoc) of the other entity 1a which stores the relevant patient information record 3a identified by the remote identifier (RID). Such an entity identifier (RLoc) may comprise a network location of the other entity 1a, for example. However, any kind of identifier can be used. The word "remote" is used here for convenience; it does not imply any physical distance between the entities. Even if the identifiers are unique across the plurality of entities, the entity identifier (RLoc) may help to make retrieving the patient data more efficient.

Alternatively, the links 7 may comprise a hyperlink or universal resource locator (URL) pointing to the corresponding patient information record. In such a case, the patient identifier assigned by the remote entity 1a may be omitted in the link 7.

As mentioned above, a further linking subsystem 6a of entity 1a may be provided for maintaining a set of links 7a of entity 1a, based on the patient identification algorithm 4a of the entity 1a. The same can be said for any other entities which are not drawn in FIG. 1. The sets of links 7,7a may also be provided by a central server (not shown), which server can maintain the sets of links 7,7a of the entities 1,1a, based on the respective patient identification algorithms 4,4a.

The entity 1 may comprise a storage for storing a local copy 15 of at least part of patient information records 3a of at least one other entity 1a. This local copy can then be used by the linking subsystem 6 and/or the patient identification algorithm 4, without having to transfer the data from the other entity 1a on demand. Consequently, only the patient information fields which are used by the patient identification algorithm 4 for matching the patient information records 3,3a need to be stored for this purpose.

Instead of local copies 15,15a, the system may comprise a central repository 17 for storing a copy of the information used by the patient identification algorithms of the plurality of entities for matching the patient information records. This alternative has been indicated by dashed symbols. It is also possible to use a combination of local copies 15,15a and a central repository 17.

An initialization subsystem 8 may be provided for initially setting up the set of links for entity 1. Similar initialization subsystems 8a may be provided for other entities 1a.

The initialization subsystem 8 may initially process substantially all available patient information records 3 of entity 1. However, patient information records 3 for which it is known beforehand that there are no corresponding patient information records at the other entities, may be skipped by the initialization subsystem 8. The initial processing of a patient information record 3 may comprise evaluating by the linking subsystem 6, in conjunction with the patient identification algorithm 4, in order to set up a set of links 7 between local patient information records 3 and patient information records 3a stored at other entities 1a.

The linking subsystem 6 may be arranged for updating the set of links 7 periodically, such as, for example, every night or every hour (e.g. during working hours) or every week or every month. Alternatively, or additionally, the linking subsystem 6 may be arranged for updating the set of links on demand or each time a new patient identifier is generated at one of the entities. To this end, a user interface may be provided to submit the demand or to create a new patient information record, which would trigger the generation of a new patient identifier. Such user interface may be provided via a workstation 18.

The patient identification algorithm 4 may be based on comparing patient demographic data (N, A, . . . ) stored in a local patient information record 3 and in a remote patient information record 3a. For example, the algorithm may comprise comparison of name, address, social security number, personal id number, tax number, age, date of birth, and/or sex. The algorithm may assign different weights (i.e., degrees of importance) to the different types of demographic information. Also, the algorithm may treat mismatches between the fields differently for different kinds of fields. All these elements of the patient identification algorithm may be set-up differently for the different entities 1, 1a. For example, the patient identification algorithm 4,4a may include thresholds which are specific for the entity 1,1a associated with the patient identification algorithm 4,4a.

As mentioned above, an entity 1 may comprise a medical workstation 18. Moreover, the entity 1 may comprise different workstations with different functionalities. One or more of such medical workstations 18 may comprise a display for displaying patient information from a patient information record 3a,19a of another entity which is linked with a patient information record 3 of the entity 1. This linking may be embodied by one of the links in the set of links 7 generated by the linking subsystem 6. For example, once a patient information record 3 of the entity 1 has been called for, the workstation 18 may display at least part of the information stored in the patient information record 3. Moreover, the workstation may look up any links 7 for the patient identifier (ID) of the displayed patient information record 3. If such a link 7 is found, the display may indicate that other information is available for this patient from another entity. Optionally, the display may indicate at which entity the information is located, based on the remote entity identifier or location (RLoc). The user may be enabled to request the additional information. Upon receiving such a request, the workstation 18 triggers a query to the remote entity 1a for patient information records 3a,19a matching the remote patient identifier (RID). The workstation 18 may then display a list of available data elements (DAT) at the remote entity 1a as listed in the patient information record 19a for the remote patient identifier (RID). For example, the patient information record 19a may comprise one or more results of prior patient examinations, such as a CT scan, or a medicine prescription. Upon request, or automatically, the workstation may retrieve one or more of the additional data elements (DAT) stored in the remote patient record 19a. The information thus retrieved may be displayed on the workstation 18, or may be subject of further processing.

Figure 2:
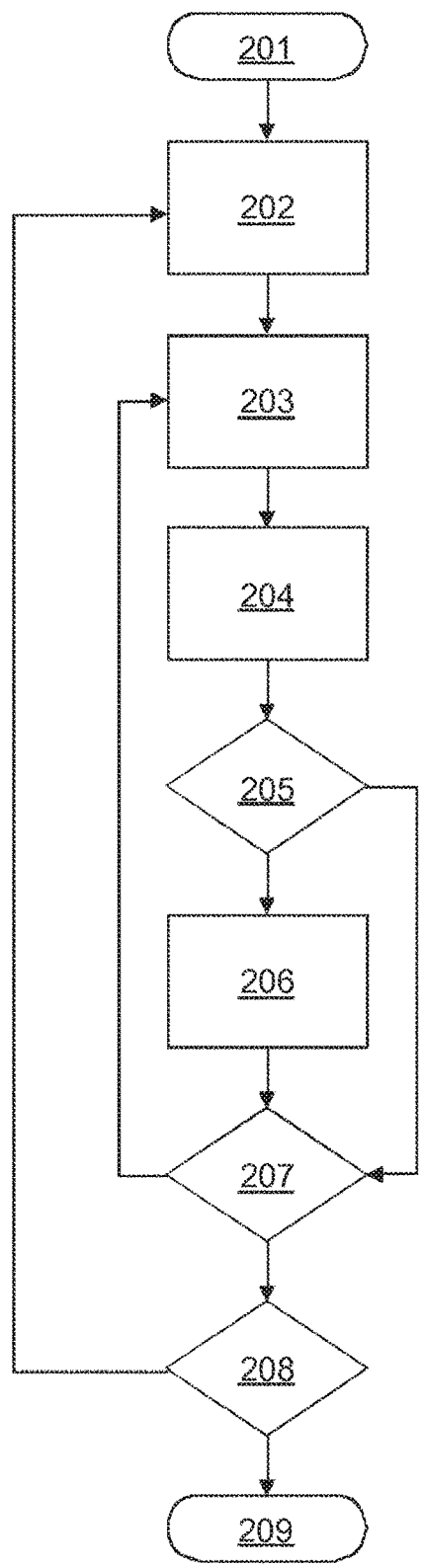
FIG. 2 is a flow chart of a method of linking corresponding patient information records at different entities.

It will be understood that the functionality of some of the elements of the system may also be viewed as steps of a process. FIG. 2 illustrates such a process of linking corresponding patient information records 3,3a at different entities 1,1a. Each entity 1,1a may have a respective patient database comprising patient information records 3,3a. Moreover, each entity 1,1a may have associated therewith a patient identification algorithm 4,4a for matching corresponding patient information records 3,3a,19,19a of the same patient at different entities 1,1a. The method may comprise the step of maintaining a set of links 7 of entity 1. This set of links 7 may link patient information records 3,19 of entity 1 with corresponding patient information records 3a,19a of another entity 1a. The method may comprise the step of establishing a link when a given patient information record 3 of entity 1 matches a corresponding patient information record 3a of entity 1a, based on the patient identification algorithm 4 of entity 1. Similarly, the method may comprise maintaining such a set of links for entity 1a and for any other entities in the system. The method may be implemented as a computer program, suitable for being executed on a server system.

FIG. 2 illustrates an example flow of a process of linking corresponding information records 3,3a at different entities 1,1a of a system as described above. The process may be triggered at step 201, for example by lapse of a particular period, or by a manual request, or by the addition of a new patient identifier in the system. After the process has been triggered, the patient information records 3 may be processed one by one. In step 202, one of these patient information records 3 of an entity 1 is selected. In the case of triggering being caused by the addition of a new patient identifier in the system, only the patient information record 3 corresponding to this new patient identifier needs to be selected and processed. In step 203, one of the other entities 1a in the system may be selected. In step 204, it may be checked whether the selected entity 1a has a patient information record 3a whose information fields match the information in the selected patient information record 3. In step 205, it is verified whether a matching patient information record 3a has been found in step 204. If no matching patient information record 3a has been found in step 204, the process proceeds with step 207. If a matching patient information record 3a has been found in step 204, in step 206, a link is established between the selected patient information record 3 and the matching patient information record 3a. This may be performed by storing a pair comprising the patient identifier found in the selected patient information record 3 and the patient identifier found in the matching patient information record 3a. An entity identifier identifying the selected other entity 1a may also be stored along with the patient identifiers. In step 207 it may be verified whether all entities have been selected for the presently selected patient information record 3. If not, the next entity may be selected by proceeding to step 203. If all entities have been selected for the presently selected patient information record 3, in step 208 it may be verified whether all local patient information records 3 have been selected. If not, the next patient information record 3 may be selected by proceeding to step 202. If yes, the process may terminate at step 209.

A person skilled in the art will appreciate that the process and system may be applied to multi-dimensional image data, e.g. to two-dimensional (2-D), three-dimensional (3-D) or four-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM). Such image data may be linked as patient data (DAT) to the patient identifier (ID) at the local entity 1 or the remote entity 1*a*, by means of a suitable patient information record 19 or 19*a*. The patient data (DAT) may also comprise laboratory results or medication prescriptions or diagnoses, for example.

The number of matches automatically rejected, accepted, or submitted for manual review may depend both on the weights associated with the different attributes during comparison, based on which the likelihood ratio may be computed, and on the chosen reject and accept thresholds. For this reason, evaluating appropriate matching weights associated with the pairs of attributes used and selecting suitable accept and reject thresholds for automatic matching may be performed to improve an identity matching implementation.

A higher reject threshold may cause a larger number of potential matches to be automatically rejected, which means that the percentage of true matches that are rejected is higher. As a result, relevant patient information may be missed. When that information is important, such as, for example, an allergy to a specific substance, or a prior cardiac event for a cancer patient receiving chemotherapy, missing it may seriously endanger the patient's health. A lower accept threshold means more potential matches are automatically accepted. In real life this means that patient information can be matched to the wrong patient, and a medical decision can be based on wrong data. Also this second type of error can be life threatening for the patient.

Hospitals can choose different trade-offs when handling data. They can choose to run the risk of missing a part of the medical history when they decide to (re)do all the tests they consider necessary, or when they have an accurate patient interviewing process in place. In this case consistency of the data is more important. On the other hand, other healthcare organizations may decide that having access to complete data is of essence, and rely on the clinicians to screen out data that is not relevant or is considered wrong.

In environments where participating institutions are only loosely coupled and remain autonomous in their governance, participating institutions may wish to retain complete control over their data and the quality process that is associated with handling it. This means for instance that if the review staff in hospital A links two patient records together, another institution, say hospital B, should still be able to do its own review on these two records and possibly (locally) overrule the link made at A. If hospital B is not able to do that, it loses its autonomy over its data and in principle cannot guarantee data consistency. As an autonomous organization, B does not need to consider and apply decisions taken at A. The same should hold for automatic matching: each institution should be able to apply its own matching process, as is the case for the system of FIG. 1 and the process of FIG. 2, when the entities are computer systems of different institutions or hospitals. When a pair of institutions, A and B, have decided on an identical matching process, the same matching process is not enforced when matching the data in institution C, because C can have its own matching process.

In the following, a non-limiting use-case will be described. Consider two institutions A and B. As described above, each of them may apply its own matching algorithm to link patient records, which results in distinct sets of links 7,7*a*. Such a set of links may be referred to as a patient registry (PR). The institutions A and B use the same demographic attributes to match the records, but they assign to those attributes different weights, WA1, . . . , WAn and WB1, . . . WBn, respectively. They also use different thresholds to automatically accept or reject matches. This may result in differences in the content of their PRs. For example, hospital A has matched the record having local identifier 115 to a record with remote identifier 371 at site B, although site B did not consider this link. Site B may have rejected this link or placed it on a manual review exception list. Similarly, when hospital C is added to the federation, A and B can use the same algorithms to match their records with records in C, or different algorithms.

Different attribute weights may be used by different entities or institutions. For example, a name that is common in a certain region should receive a different matching weight than a very uncommon name in that region, and matching across regions may mean using different weights. An age of 93 years old should have a lower matching weight between two geriatrics clinics than when matching data in two large university hospitals. In the following, a non-limiting example use case is described, involving a comparison of the demographic information captured by two records in two hospitals A and B. The record stored in hospital A has patient name "Jansen, Peter", age "53", address "Addr1", and gender "Male", whereas the record stored in hospital B has patient name "Janssen, Peter" (with double s), age 53, address "Addr2", and gender "Male". Both names (Peter Jansen and Peter Janssen) occur quite frequently in the Netherlands. Depending on A and B the decision of whether to match the two records could be quite different. For example, two hospitals in the Netherlands would have low weights for the name, because both names are existing, rather common names. This could cause an automatic reject of the match as the addresses are different. If the age were 93 in both patient records, the weight of the match would increase for two general-purpose hospitals as not so many of their patients would be 93 years old, but not for two geriatrics clinics, because they would have more elderly patients. If A and B were two hospitals in France, the weight of the uncommon name would be much higher and the records would probably be submitted for manual review.

It may also be the case that two healthcare organizations take different approaches, resulting in different matching, with respect to each other. For example, an emergency hospital generally would be less interested to retrieve older unrelated data from the patient's community hospital, since they treat emergency cases and re-do most of the tests; moreover, when the patient was transferred to the emergency hospital he most likely arrived with all relevant data. Their matching process would be very conservative, aiming at a small exception lists (that needs to be manually reviewed), and having a high reject threshold. On the other hand the community hospital would probably need to have access to information about the patient's emergency episode as they are going to see the patient in the future, so they would prefer to have more, rather than less, information from the remote site.

The system described herein can, instead of building a single global patient registry (PR) containing all the links considered valid for an entire federation, build own PRs and maintain them for every institution, said PRs thus serving as a local ground truth with respect to that institution. Each institution can maintain its own PR locally, or at the Common Federation Services. The advantages of maintaining the PRs locally are that no wide-area communication is necessary to search the PR and that the information in the PR is available even when the site becomes temporarily disconnected from the federation. Of course, a mechanism can be put in place to update the information in the PRs as new patients are seen (this can be done daily, weekly, etc).

Local sites can choose to apply a different matching process for each other site in the federation (algorithm, weights and thresholds). The result of the matching may comprise a set of links that connect patient records in the local system to patient records at another site. The computer system at such a site can be an entity of the system described above.

Instead of building a common, federation-wide PR, each local PR may store for each identifier of a patient known locally, all the identifiers of records matched as belonging to that patient at other sites together with the identifiers of the sites holding those records. As the matching is only valid for the local site, the fact that the links were obtained through different matching processes does not affect the consistency of the data. The local system has the autonomy to choose what data to retrieve from other sites without needing to take into account the matching decisions at those sites. Site A may decide to link an own record with PID=123 with a record with PID=456 at site B, but not to a record with PID=789 at site C. The fact that site B might have linked PID=456 with PID=789 has no bearing on the decision at A.

The total amount of data stored in the local PRs may be larger than the amount of data that would have been stored in a single global PR, but each local PR may be significantly smaller than the global PR as it only needs to store data concerning the patients known at the local site. Currently, on average below 20% of patients have data at more than one site, so also the percentage of records that are stored in the PR at more than one site may be below 20%. This percentage is only an example. It may differ from situation to situation and can fluctuate over time.

Additionally, each site may maintain a database containing the demographic data used for matching for all the remote sites (or at least some of the remote sites, e.g. the most important ones) in the federation. If instead of building them at each site, all these distinct PRs are maintained at a common site, which may be called a Federation Services site, a single demographics database may be prepared, containing all the relevant demographics (i.e. those used for matching) for all sites. Alternatively, an entity may query the databases of the other entities separately. The patient registry (PR) may record the data which is necessary to link local patient identifiers with remote patient identifiers.

In the following it is assumed that each site maintains its own PR. However, what is described below can be adapted by the skilled person to the case of a central PR and to the case of individually querying the other entities. When a new record for a patient previously unknown is added at site A, a new record in the local PR may be created, initially holding only the new local PID, and when desired also the locally known demographics of that patient. Next, based on the demographics of the new patient all demographic data potentially relevant may be pulled from each other site and the corresponding matching algorithm may be run. When the local demographic data is stored in the PR, the current site can match its new patient demographics directly against demographic data in each remote PR, and there is no need to query the remote systems. As an alternative the local site can send the demographic info to the remote site and ask that site to provide all the potential matches with demographic data in its PR. Next, the local site may perform the matching algorithm on the data returned from the remote site, and store in the PR entry of the new patient at the local site all remote identifiers considered as matches and the identifier of the remote site holding them.

As matching links may be specific for each site, when a new patient record is introduced at site A and the matching is carried out, remote sites will not be automatically aware of the new entry. Also, the locally established links may not be relevant for them and may not be adopted. However, sites may need to know of new records entered at other sites in the federation, as those can match with own records and provide relevant information. This can be achieved by letting each site A notify all the other sites when a new patient record is created and a new identifier is assigned to it. This can be efficiently done when site A carries out its identity matching to the data in each remote site. When site A sends out the demographics for the new patient to site B and requests demographics of potentially matching records, the locally-assigned identifier of the new record can be sent as well. This way, based on the demographics received, site B can also match the new record at site A against the records in its own PR (at site B) and when it finds a match to an own record (which is an entry in its PR), add the patient identifier received from A and a reference to A to the local entry. For each new record entered, there may be a single communication step between the local site and all the other sites in the federation, during which demographic data and/or patient identifiers are exchanged. After that the new record may be matched against existing records at each site.

This way, all PRs can be kept up-to-date when new records are added to local sites, even though the matching processes are local to each site.

The following describes a process enabling building and updating the PRs. It is assumed that there is a federation of N sites (where a site corresponds to an entity of the system as described above).

1. Each site may build its own initial PR all at once, like a big-bang, or more gradually, according to the following steps:
a. Retrieve and store demographic data (e.g. name, age, gender, address) and the IDs for the patients at the other N−1 sites. This information may also be used during normal operation so it may be preserved in a demographics database.
b. Match the demographics of patients at own site against the demographics of the patients at the remote sites, using own algorithms, weights and thresholds for matching (all these can be different for each pair of sites).
c. Store in own PR the pairs of records identified as automatic matches, for example as triplets of (local patient ID, remote site ID, remote patient ID). Other relevant information, such as a time stamp, can be stored as well.
d. Build the list of exceptions for manual review with the record pairs that could not be automatically matched or rejected (i.e. fell between the two thresholds).
e. Enable an operator to review the exception list and add pairs of records asserted as matches to the PR.
2. Each site may execute the following steps during normal operation:
a. When a new patient is registered at the local site, run the matching for her or his demographics against the records in the demographics database.
b. When matches are found, the triplet (local patient ID, remote site ID, remote patient ID) is added to the PR.

c. When a potential match is found (between the two thresholds) the triplet is added to the exception list for manual review.

d. Periodically (e.g., once-a-day, once-a-week):

i. Retrieve the relevant demographics for the patients registered at the other sites. Match own patient demographics against the demographics of newly retrieved remote patients.

ii. When matches are found, the triplet (local patient ID, remote site ID, remote patient ID) is added to the PR.

iii. When a potential match is found (between the two thresholds) the triplet is added to the exception list for manual review.

iv. Store the newly retrieved demographics in the demographics database.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system that links patient information records, of a same patient, that are stored at different facilities, comprising:

a plurality of facilities, each facility including:

one or more patient databases comprising patient information records;

a facility specific patient identification algorithm, stored in computer memory, that matches patient information records, of the same patient, located at its facility of the plurality of facilities with the patient information records, of the same patient, located at other facilities of the plurality of facilities;

a linking subsystem, implemented via a microprocessor, that maintains a set of links between its facility and the other facilities of the plurality of facilities, and each link of the set of links represents a facility specific match and each link is stored in computer memory, wherein each link comprises an entity identifier;

wherein the linking subsystem of a first facility of the plurality of facilities links patient information records, of the same patient, located at the first facility with corresponding patient information records, of the same patient, located at a second facility of the plurality of facilities creating a first link of the set of links of the first facility in response to a first facility specific patient identification algorithm of the first facility matching the patient information record, of the same patient, located at the first facility with a corresponding patient information record, of the same patient, located at the second facility;

wherein the linking subsystem of the second facility of the plurality of facilities links patient information records, of the same patient, located at the second facility with corresponding patient information records, of the same patient, located at the first facility of the plurality of facilities creating a first link of the set of links of the second facility in response to a second facility specific patient identification algorithm of the second facility matching the patient information record, of the same patient, located at the second facility with the corresponding patient information record, of the same patient, located at the first facility, wherein the first facility specific patient identification algorithm and the second facility specific patient identification algorithm are different, wherein the first link of the first facility and the first link of the second facility are different links;

wherein at least the first facility locally stores a copy of at least a sub-set of the corresponding patient information records, of the same patient, located at the second facility of the plurality of facilities, and the facility specific patient identification algorithm of the first facility employs the locally stored copy to match the patient information records from the second facility; and wherein the facility specific patient identification algorithm of the first facility matches the patient identification records between the patient information record of the same patient of the second facility and the patient record of the same patient of a third facility with at least one of a different threshold for acceptance and different weighted attributes.

2. The system according to claim 1, wherein the links provide an association between locally-assigned patient identifiers of the same patient at different facilities.

3. The system according to claim 1, further comprising:
a central repository that stores a copy of information used by the facility specific patient identification algorithms of each of the plurality of facilities to match the patient information records according to each of the plurality of facilities.

4. The system according to claim 1, comprising:
an initialization subsystem for initially setting up the set of links for the first facility, processing substantially all available patient information records of the first facility and corresponding patient information records received by the first facility for each other facility of the plurality of facilities, each link in the set of links representing a link to patient information records at a corresponding facility.

5. The system according to claim 1, wherein each link is a single directional match from a local patient identification to a remote patient identification between the facility and a remote facility and includes the local patient identification, a remote facility identification, and the remote patient identification.

6. The system according to claim 1, wherein the linking subsystem of the first facility updates the set of links of the first facility on demand or each time a new patient identifier is generated at one of the facilities.

7. The system according to claim 1, wherein the facility specific patient identification algorithm of the first facility and facility specific patient identification algorithm of the second facility match patient demographic data differently by at least one of an attribute and a weight of an attribute.

8. The system according to claim 7, wherein the demographic data attributes includes at least one of: a name, an address, a social security number, a personal identification number, a tax number, an age, a date of birth, or a gender.

9. The system according to claim 1, wherein the patient identification algorithm includes thresholds for at least one of acceptance of a match or rejection of a match which are specific for the facility associated with the patient identification algorithm.

10. A medical workstation which is part of the first facility according to claim 1, the medical workstation comprising a display for displaying patient information from a patient information record of at least the second facility which is linked with a patient information record of the first facility.

11. A computer-implemented method of linking corresponding patient information records at a plurality of facilities, each facility having respective patient databases comprising patient information records, each facility having associated therewith a patient identification algorithm for matching corresponding patient information records of a same patient at different entities, the method comprising:

maintaining, via a microprocessor, a first set of links of a first facility of the plurality of facilities, the first set of links linking patient information records of the first facility with corresponding patient information records of other facilities, a first link of the first set of links being established when a given patient information record of the first facility matches a corresponding patient information record of another facility, based on a first patient identification algorithm of the first facility, and each link in the set of links representing a facility specific link to the corresponding patient information record of another facility of the plurality of facilities and each link is stored in computer memory;

maintaining, via the microprocessor, a second set of links of a second facility of the plurality of facilities, the second set of links linking patient information records of the second facility with corresponding patient information records of the other facilities, a second link of the second set of links being established when a given patient information record of the second facility matches a corresponding patient information record of another facility, based on a second patient identification algorithm of the second facility, wherein the first patient identification algorithm of the first facility creates the first link and the second patient identification algorithm of the second facility creates the second link;

wherein the first patient identification algorithm of the first facility and the second patient identification algorithm of the second facility are different;

wherein the first link and the second link are different links;

wherein at least the first facility locally stores a copy of a sub-set of the corresponding patient information records, of the same patient, located at the second facility of the plurality of facilities, and the facility specific patient identification algorithm of the first facility employs the locally stored copy to match the patient information records from the second facility; and wherein the facility specific patient identification algorithm of the first facility matches the patient identification records between the patient information record of the same patient of the second facility and the patient record of the same patient of a third facility with at least one of a different threshold for acceptance and different weighted attributes.

12. A computer program product comprising instructions that causes the microprocessor to perform the method according to claim 11.

13. The computer-implemented method according to claim 11, wherein the set of links of the first facility and the patient identification algorithm of the first facility are located in computer hardware memory at the first facility.

14. The computer-implemented method according to claim 13, wherein the second set of links of the second facility of the plurality of facilities and the second patient identification algorithm of the second facility are located in computer hardware memory at the second facility.

15. The computer-implemented method according to claim 11, wherein the set of links of the first facility and the patient identification algorithm of the first facility are not located in a Federation Services site.

16. The system according to claim 1, wherein each link in the set of links includes a local patient identification, a remote facility identification, and a remote patient identification; and the remote facility identification identifies one of the plurality of facilities.

\* \* \* \* \*